US012559716B2

(12) United States Patent
Kang et al.

(10) Patent No.: US 12,559,716 B2
(45) Date of Patent: *Feb. 24, 2026

(54) MICROCAPSULES CONTAINING NATURAL OIL AND PREPARATION METHOD THEREFOR

(71) Applicant: Korea Research Institute of Chemical Technology, Daejeon (KR)

(72) Inventors: Sun Woong Kang, Daejeon (KR); Hye Eun Shim, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 712 days.

This patent is subject to a terminal disclaimer.

(21) Appl. No.: 17/283,518

(22) PCT Filed: Nov. 12, 2019

(86) PCT No.: PCT/KR2019/015349
§ 371 (c)(1),
(2) Date: Apr. 7, 2021

(87) PCT Pub. No.: WO2020/101327
PCT Pub. Date: May 22, 2020

(65) Prior Publication Data
US 2021/0388314 A1    Dec. 16, 2021

(30) Foreign Application Priority Data

Nov. 13, 2018    (KR) ......................... 10-2018-0139190

(51) Int. Cl.
*B01J 13/08* (2006.01)
*C12N 5/00* (2006.01)
*C12N 5/077* (2010.01)

(52) U.S. Cl.
CPC ........... *C12N 5/0075* (2013.01); *B01J 13/08* (2013.01); *C12N 5/0657* (2013.01); *C12N 2531/00* (2013.01); *C12N 2533/54* (2013.01); *C12N 2533/70* (2013.01); *C12N 2533/80* (2013.01)

(58) Field of Classification Search
None
See application file for complete search history.

(56) References Cited

U.S. PATENT DOCUMENTS

| | | | |
|---|---|---|---|
| 5,051,304 A | 9/1991 | David | |
| 5,693,343 A | 12/1997 | Reid | |
| 7,255,874 B1 | 8/2007 | Bobo | |
| 8,557,288 B2 | 10/2013 | Elbert | |
| 11,077,032 B2 | 8/2021 | Goutayer | |
| 11,160,761 B2 | 11/2021 | Brahms | |
| 2007/0042184 A1* | 2/2007 | Coyne | A01N 63/50 |
| | | | 428/402.2 |
| 2009/0087569 A1* | 4/2009 | Fan | C08B 37/0072 |
| | | | 427/372.2 |
| 2012/0076839 A1* | 3/2012 | Chan | A61K 8/84 |
| | | | 424/47 |
| 2012/0269748 A1* | 10/2012 | Tamura | A61K 8/892 |
| | | | 424/59 |
| 2014/0349396 A1 | 11/2014 | West | |
| 2016/0083690 A1 | 3/2016 | Birch | |

FOREIGN PATENT DOCUMENTS

| | | |
|---|---|---|
| CN | 1485094 C | 3/2004 |
| CN | 1641017 C | 7/2005 |
| CN | 102952274 B | 3/2013 |
| JP | 2007-215519 A | 8/2007 |
| KR | 10-0871-6520000 | 12/2008 |
| KR | 10-2012-0089329 | 8/2012 |
| KR | 10-2013-0138240 | 12/2013 |
| KR | 10-2014-0126972 | 11/2014 |
| KR | 10-2016-0077757 | 7/2016 |
| KR | 10-1655-4070000 | 9/2016 |
| KR | 10-2016-0137780 | 12/2016 |
| WO | 2015/173425 A1 | 11/2015 |

OTHER PUBLICATIONS

McLain (International Journal of Toxicology, 27(Suppl. 4):83-106. 2008, DOI: 10.1080/10915810802550611) (Year: 2008).*
Marques da Silva et al (LWT—Food Science and Technology 90 (2018) 412-417, https://doi.org/10.1016/j.lwt.2017.12.057, Available online Dec. 28, 2017) (Year: 2017).*
Gasperini et al (J. R. Soc. Interface 11: 20140817. DOI: 10.1098/rsif.2014.0817) (Year: 2014).*

(Continued)

*Primary Examiner* — Peter Paras, Jr.
*Assistant Examiner* — Khoa Nhat Tran
(74) *Attorney, Agent, or Firm* — Barry L. Davison; Davis Wright Tremaine LLP

(57) ABSTRACT

The present invention relates to microcapsules comprising natural oil and, more specifically, to microcapsules which contain gelatin, natural polymers, oil, and an oil thickener and have enhanced mechanical properties, and a preparation method therefor. The microcapsules comprising natural oil according to the present invention have remarkably enhanced mechanical properties and retention properties, and when co-cultured with cells, the microcapsules provide the effect of inducing maturation of the cells, and thus may be used in various fields of microcarriers, cell cultures, and co-culture systems.

5 Claims, 7 Drawing Sheets

(56)                 References Cited

OTHER PUBLICATIONS

International Search Report dated Feb. 24, 2020, issued in International Patent Application No. PCT/KR2019/015349, filed Nov. 12, 2019, 4 pages.

Antonov, S.A., et al., "The Current State of Development of Greases," Chemistry and Technology of Fuels and Oils 57(2):279-288, 2021.

Arancibia, C., et al., "Application of CMC as Thickener on Nanoemulsions Based on Olive Oil: Physical Properties and Stability," International Journal of Polymer Science 2016:1-10, Article ID 6280581, Oct. 18, 2016.

Campàs, O., et al., "Quantifying Cell-Generated Mechanical Forces Within Living Embryonic Tissues," Nature Methods 11:183-189, 2014.

Gonçalves, N.D., et al. "Comparison of Microparticles Produced With Combinations of Gelatin, Chitosan and Gum Arabic," Carbohydrate Polymers 196:427-432., 2018.

Jensen, C., and Y. Teng, "Is It Time to Start Transitioning From 2D to 3D Cell Culture?," Frontiers in Molecular Biosciences 7:33, Mar. 6, 2020.

Karmakar, G., et al., "Chemically Modifying Vegetable Oils to Prepare Green Lubricants," Lubricants 5(4):44, 2017.

Martín-Alfonso, M.A., et al. "Impact of Vegetable Oil Type on the Rheological and Tribological Behavior of Montmorillonite-Based Oleogels," Gels 8(504):1-15, 2022.

Mousa, M., et al., "Clay Nanoparticles for Regenerative Medicine and Biomaterial Design: A Review of Clay Bioactivity," Biomaterials 159:204-214, 2018.

Nirmala, D., et al. "Gelatin and Gelatin-Polyelectrolyte Complexes: Drug Deliver," Research Gate <https://www.researchgate.net/publication/293763161, Jan. 2016, pp. 3557-3569.

Shim, J.-K., "Three-Dimensional Co-Culture of Cells Using the Iron Oxide Containing Silk Fibroin Microcapsules Based on Magnetic Levitation," Department of Bioengineering and Technology, Graduate School, Kangwon National University, Feb. 2017, 86 pages.

Tuveson, D., and H. Clevers, "Cancer Modeling Meets Human Organoid Technology," Science 364:952-955, 2019.

Xiong, R., et al., "Naturally-Derived Biopolymer Nanocomposites: Interfacial Design, Properties and Emerging Applications," Materials Science and Engineering: R: Reports 125:1-41, 2018.

Yamaguchi, M., ed., "Drosophila Models for Human Diseases," Springer, Jun. 27, 2018.

International Search Report dated Mar. 3, 2020, issued in International Patent Application No. PCT/KR2019/095041, filed Nov. 12, 2019, 4 pages.

International Search Report dated Mar. 4, 2020, issued in International Patent Application No. PCT/KR2019/095042, filed Nov. 12, 2019, 4 pages.

Sato, N., et al., "Lipid Metabolism and Potentials of Biofuel and High Added-Value Oil Production in Red Algae," World Journal of Microbiology and Biotechnology 33(74):1-11, Mar. 2017.

Suflita, M., et al., "Heparin and Related Polysaccharides: Synthesis Using Recombinant Enzymes and Metabolic Engineering," Applied Microbiology and Biotechnology 99:7465-7479, Jul. 2015.

* cited by examiner

【Figure 1a】
A. Oil thickener non-added group
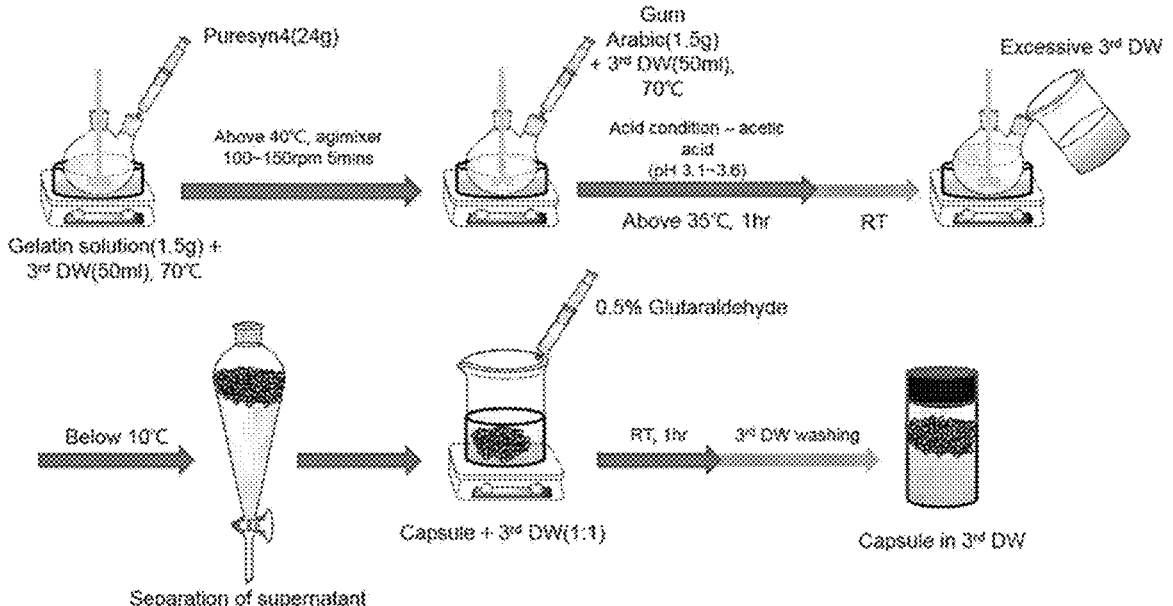
【Figure 1b】
B. Oil thickener added group
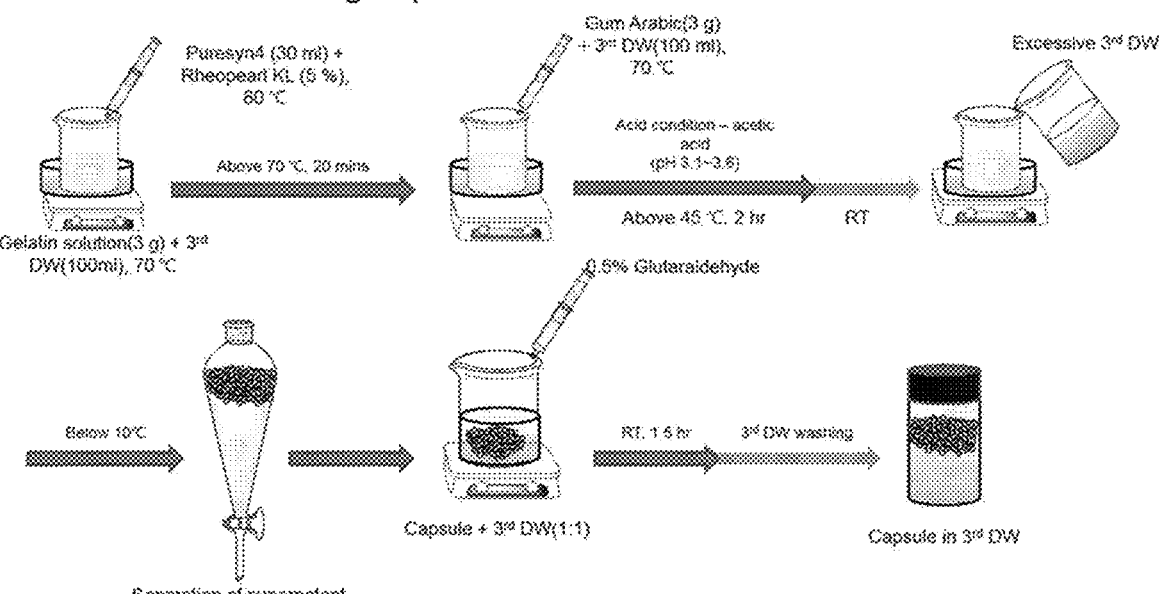

【Figure 2】
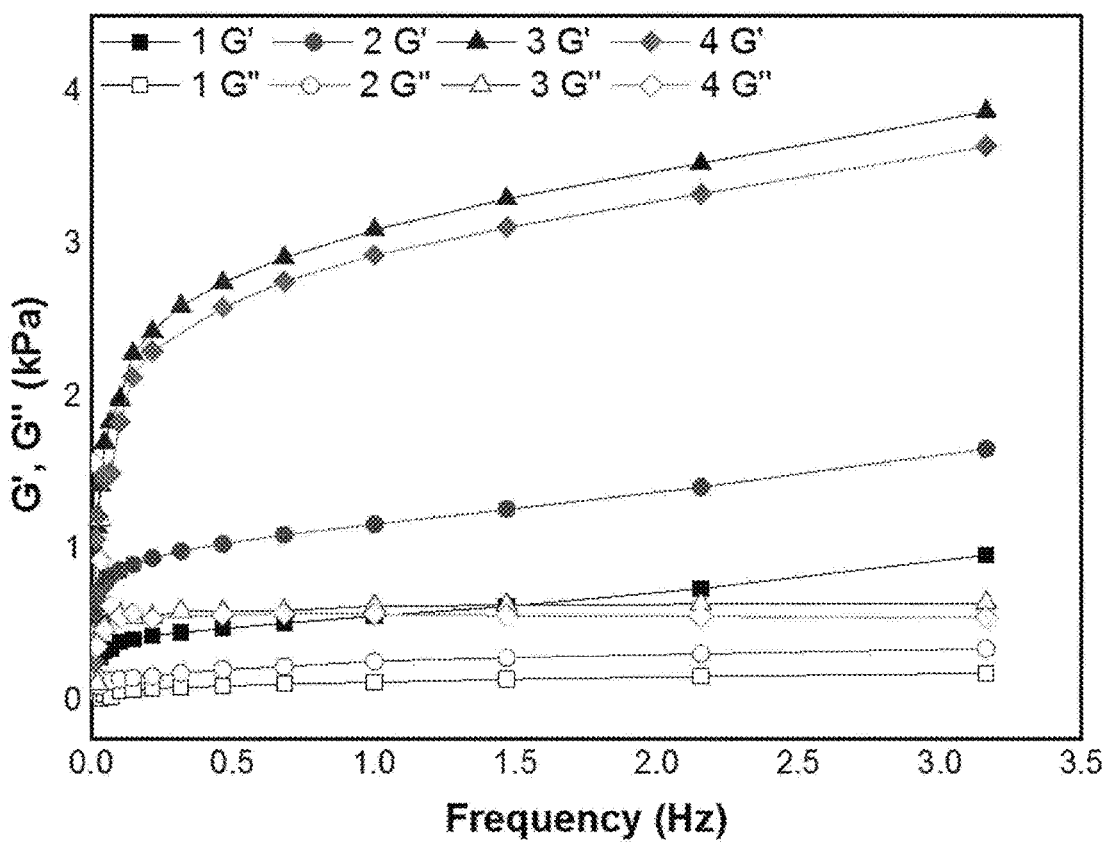
Mechanical properties. Frequency of 0.01 to 5 Hz,
Strain of 0.01% at 24°C 【Figure 3】
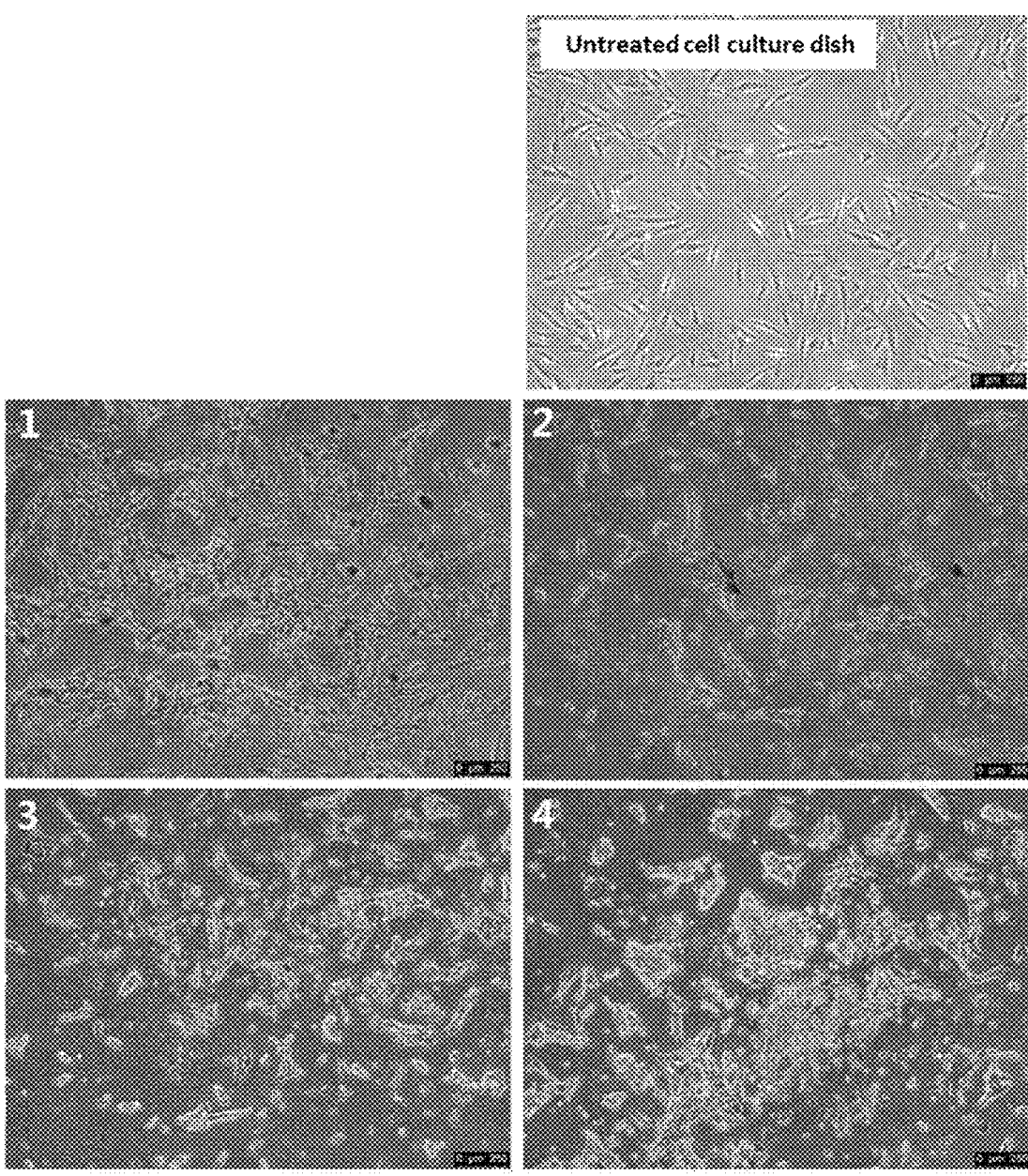

【Figure 4】
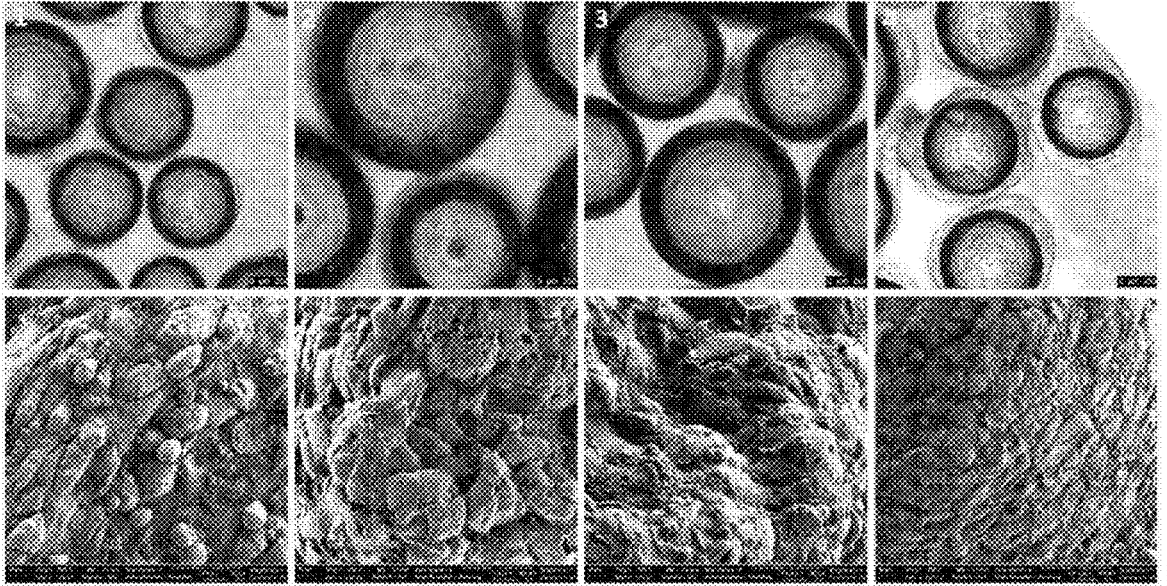
Figure 5】
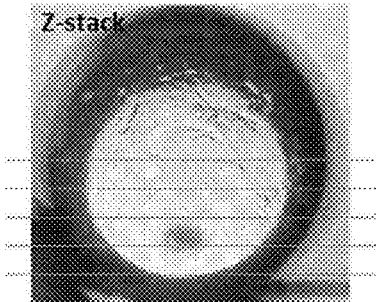
Checking cell viabilities of cardiomyocytes adhered to the surface of squalane through live-dead assay
(Z-stack, Confocal)
Green : Live, Red : Dead
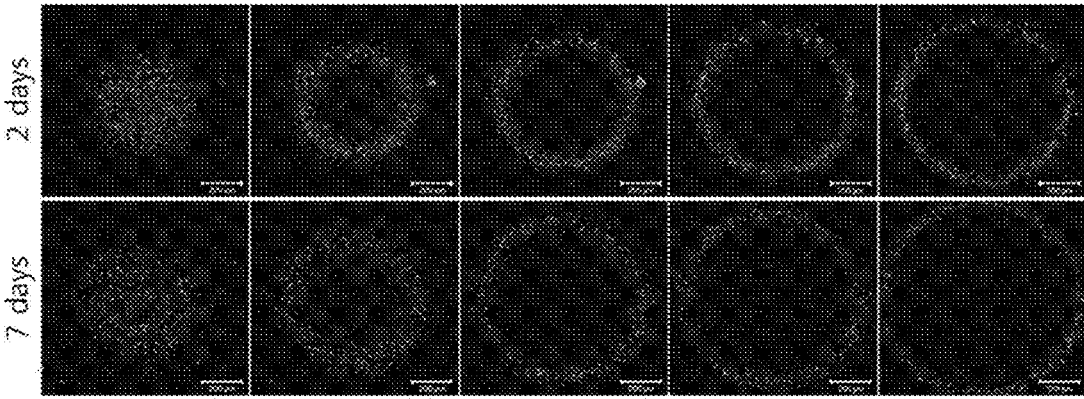

【Figure 6】
2D culture
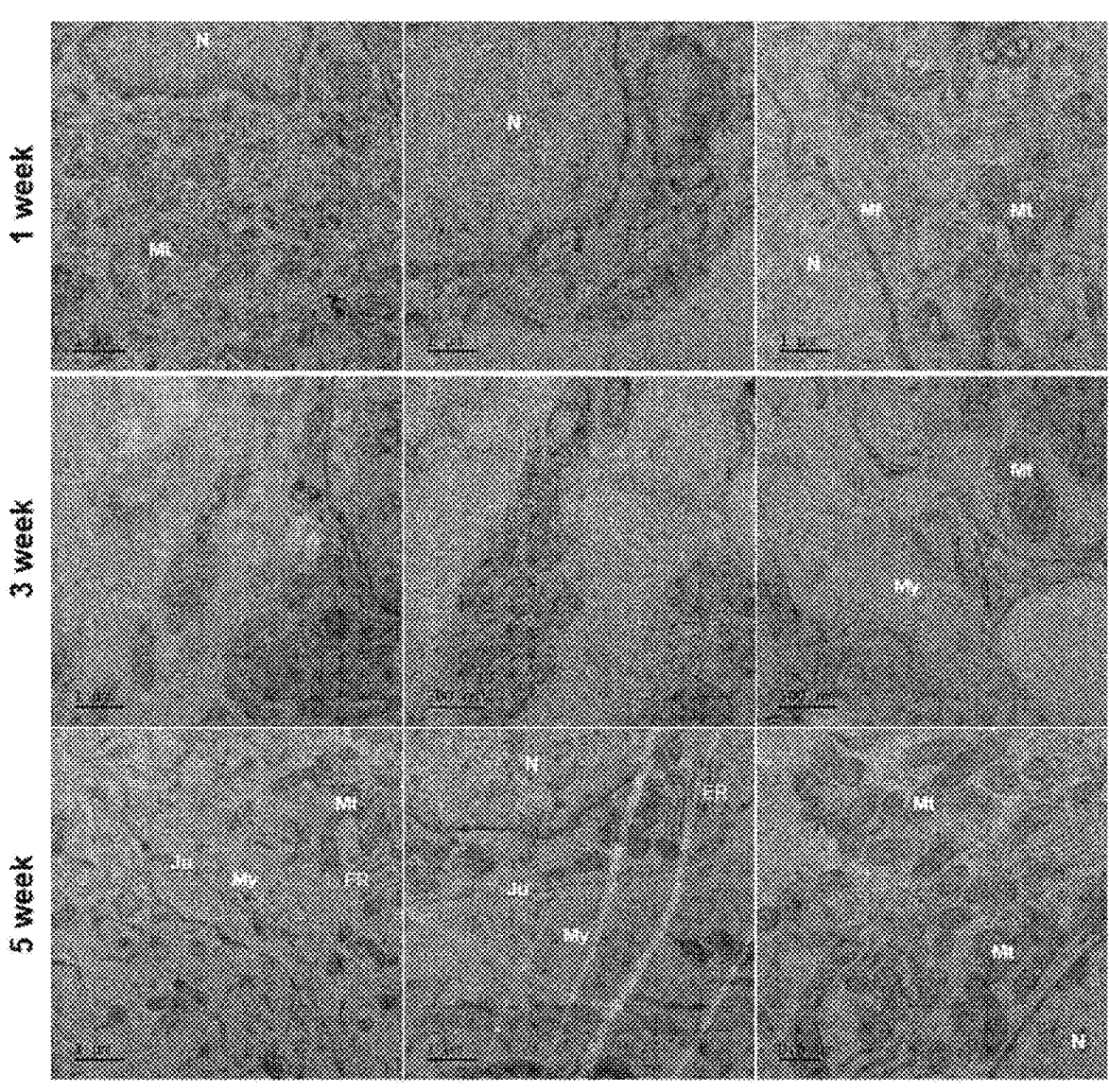

【Figure 7】
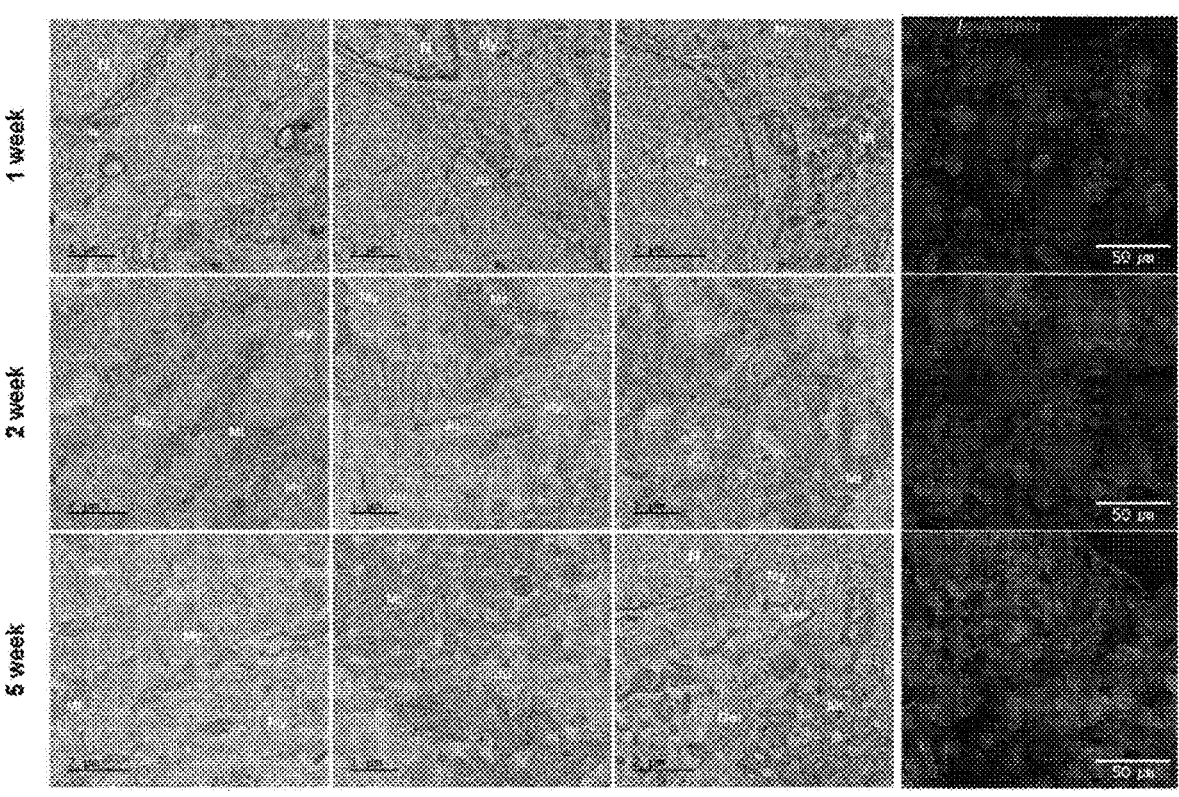

【Figure 8】
Experimental group 4 (Oil thickener untreated)
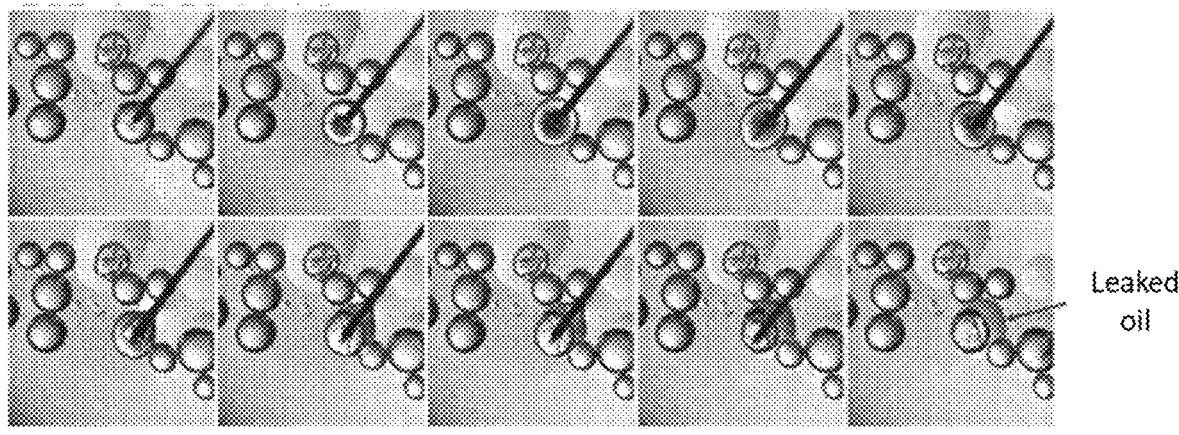
Leaked oil
Experimental group 10 (Oil thickener treated)
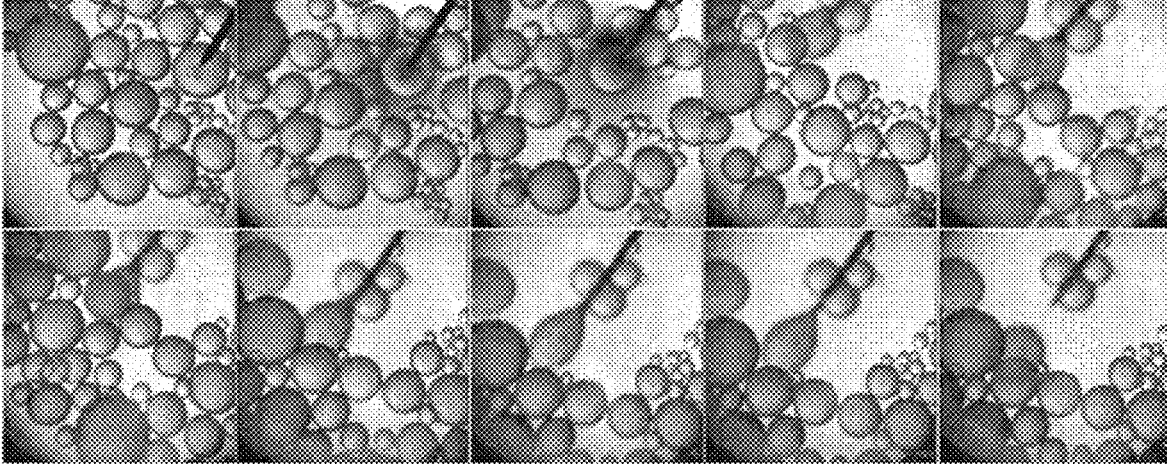

MICROCAPSULES CONTAINING NATURAL OIL AND PREPARATION METHOD THEREFOR

TECHNICAL FIELD

The present invention relates to microcapsules comprising a natural oil, and more particularly, to microcapsules containing gelatin, a natural polymer, an oil, and an oil thickener and having enhanced mechanical properties, and a preparation method thereof.

BACKGROUND ART

Although it does not exist naturally, gelatin is a material obtained by hydrolyzing collagen, i.e., a protein which is present in the tissues of living organisms. Gelatin is close to colorless and has little taste or fragrance, and is variously used in varieties of food additives. Gelatin has a molecular weight of about 35,000 to 40,000, and is mainly comprised of glycine, proline, hydroxyproline, and glutamic acid. Gelatin, as a biomaterial excellent in biocompatibility, is a natural polymer that is free of toxicity, is biodegradable in the body, and has poor antibody induction. Gelatin is a material which is used for various purposes such as artificial skin, a contact lens, a drug delivery carrier, etc., and is applicable to various other fields. In addition, gelatin, as a typical thermoreversible gel, exists in a sol state at a specific temperature or higher, but becomes a gel form at the specific temperature or lower. Although gelatin may form a physical gel even without a special crosslinking agent, gelatin has a problem that it has weak strength as in a general hydrogel. A gelatin gel formed by low temperatures is, as a physical gel, made by weak bonds. It has been known that a crosslinking agent is used so as to supplement strength of gelatin, and the amine group of proteins is involved in chemical crosslinking of gelatin.

Meanwhile, microcapsules mean ultrafine particles which have sizes of several microns to hundreds of microns, and in which a liquid phase or solid phase material forming an inner part (core) is surrounded by a polymer material or the like forming an outer part (wall). Such microcapsules may be used in preventing the degeneration of a core mated al with respect to an external environment (for example, oxygen or moisture), constantly maintaining the transfer rate of material such as a sustained release drug or an air freshener, or converting a material used as the core from a liquid from to a solid form. The microcapsules, as a generic technology used in various fields such as medicine and medical supplies, paints, electronic industry, cosmetic products, etc., have been used as the best tool of maintaining the initial potency of the drug when the microcapsules are used especially in the medicine and medical supplies and the cosmetic products.

DISCLOSURE

Technical Problem

Accordingly, the present inventors have completed the present invention by developing natural oil-containing microcapsules with remarkably enhanced mechanical properties, and confirming uses of the microcapsules.

Therefore, an object of the present invention is to provide microcapsules containing gelatin, a natural polymer, an oil, and an oil thickener, and a preparation method thereof.

Technical Solution

In order to achieve the aforementioned object, the present invention provides microcapsules containing gelatin, a natural polymer, an oil, and an oil thickener.

Furthermore, the present invention provides a preparation method of the microcapsules comprising the steps of preparing a gelatin solution containing gelatin, an oil, and an oil thickener, preparing a natural polymer solution, mixing the gelatin solution and the natural polymer solution, adjusting pH of the mixture, and cooling the pH-adjusted mixture.

Advantageous Effects

Microcapsules comprising a natural oil according to the present invention have remarkably increased mechanical properties and retention properties, have the effect of inducing maturation of the cells when co-culturing the microcapsules with cells, and thus may be used in various fields of microcarriers, cell cultures, and co-culture systems.

DESCRIPTION OF DRAWINGS

FIG. 1 illustrates a preparation method of gelatin oil capsules according to the present invention (A: when an oil thickener is not added, B: when the oil thickener is added).

FIG. 2 shows elastic modulus measurement results of gelatin oil capsules according to the present invention.

FIGS. 3 and 4 are views showing results of observing cultured cells through an optical microscope, a scanning electron microscope (SEM), and a transmission electron microscope (TEM) after co-culturing gelatin oil capsules according to the present invention and cardiomyocytes.

FIG. 5 is a view showing results of checking the cellular viability of cardiomyocytes co-cultured with gelatin oil capsules according to the present invention through live-dead assay.

FIG. 6 is a view showing results of observing, through a TEM, results of culturing cardiomyocytes by a conventional method.

FIG. 7 is a view showing results of observing, through a TEM and a fluorescence microscope, results of co-culturing gelatin oil capsules according to the present invention and cardiomyocytes.

FIG. 8 is a view showing results of comparing retention properties of gelatin oil capsules according to the present invention depending on whether an oil thickener has been added or not.

MODES OF THE INVENTION

Hereinafter, the present invention will be described in detail.

According to an aspect of the present invention, the present invention provides microcapsules comprising a natural oil, the microcapsules which contain gelatin, a natural polymer, an oil, and an oil thickener.

In the present invention, a "natural polymer" means a polymer material which is present in nature or produced by living things, and the natural polymer plays roles of oxidation prevention and stabilization of oil inside microcapsules.

Although examples of the natural polymer may include Arabic gum, hyaluronic acid, guar gum, pectin, xanthan gum, locust bean gum, tamarind gum, tragacanth gum, gum ghatti, locust bean gum, Konjac gum, agar, Carragheenan, furcellaran, gellan, etc., the natural polymer is not limited thereto.

In an embodiment of the present invention, the gelatin and the natural polymer are preferably mixed at a weight ratio of 1:0.1 to 1.

According to a preferred embodiment of the present invention, the natural polymer is preferably Arabic gum, more preferably a mixture of Arabic gum and hyaluronic acid, and Arabic gum and hyaluronic acid are more preferably mixed at a weight ratio of 1:9 to 9:1 in the mixture of Arabic gum and hyaluronic acid.

In the present invention, the oil may be one or more selected from the group consisting of olive oil, camellia oil, castor oil, palm oil, Jojoba oil, almond oil, grapeseed oil, herbal oil, rose oil, coconut oil, moringa oil, rice bran oil, apricot kernel oil, sunflower oil, meadowfoam seed oil, Abyssinian oil, and squalane, and is not limited thereto. In an embodiment of the present invention, the oil is preferably squalane. The squalane may be phytosqualane.

In the present invention, "Phytosqualane", as a natural squalane replacing animal squalane, is produced by adding hydrogen to squalane extracted from vegetable oil. Phytosqualane has a function of preventing evaporation of moisture, and microcapsules prepared by adding phytosqualane have the advantage of maintaining moisture in the capsules for a long time.

In the present invention, a "thickener", as a material of increasing the viscosity of a solution, is referred to as a thickener or a thickening stabilizer. In addition, since the solution appears to be sticky when adding the thickener to the solution, there is a case that the thickener is written as a thickening agent as it seems as if the solution is concentrated. In the present invention, the thickener has been used in order to enhance the viscosity of an oil contained inside microcapsules.

In an embodiment of the present invention, the oil thickener may be one or more selected from Bentone gel, hydrogenated polyisobutene, dextrin palmitate/ethylhexanoate, and dextrin palmitate, and may be more preferably dextrin palmitate. The oil thickener may also be one or more selected from Bentone gel, Versagel ME 750, Rheopearl TT, and Rheopearl KL that are commercially available.

In the present invention, although the oil thickener may be contained in an amount of 1 to 15 wt %, preferably 2 to 10 wt %, more preferably 4 to 6 wt %, and most preferably 5 wt % with respect to the weight of the oil, the content of the oil thickener is not limited thereto.

Microcapsules comprising a natural oil, according to the present invention, have the effects of allowing the cells to form spheres when the microcapsules are co-cultured with cells, and maturing cultured cells by remarkably increasing mechanical properties compared to microcapsules prepared by a conventional method.

According to other aspect of the present invention, the present invention provides a preparation method of microcapsules comprising a natural oil, the preparation method comprising: a step (a) of preparing a gelatin solution containing gelatin, an oil, and an oil thickener; a step (b) of preparing a natural polymer solution; a step (c) of mixing the gelatin solution and the natural polymer solution; a step (d) of adjusting pH of the mixture prepared in the step (c); and a step (e) of cooling the pH-adjusted mixture of the step (d).

Specifically, a preparation method of microcapsules according to the present invention is shown in FIG. 1.

Although the oil thickener of the step (a) may be contained in an amount of 1 to 15 wt %, preferably 2 to 10 wt %, more preferably 4 to 6 wt %, and most preferably 5 wt % with respect to the weight of the oil, the content of the oil thickener is not limited thereto.

Although the natural polymer solution of the step (b) is preferably a mixture obtained by mixing Arabic gum and hyaluronic acid at a weight ratio of 1:9 to 9:1, the natural polymer solution is not limited thereto.

The step (d) preferably comprises adjusting pH of the mixture of the gelatin solution and the natural polymer solution to 3.1 to 3.6.

Furthermore, the step (e) preferably comprises adding distilled water corresponding to 3 to 5 times the pH-adjusted mixture to the pH-adjusted mixture, stirring the distilled water in the pH-adjusted mixture, and cooling the stirred material so that temperature of a stirred material becomes 5° C. to 15° C.

Hereinafter, the present invention will be described in more detail through Examples. These Examples are only for the purposes of illustrating the present invention, and it should be obviously construed by those skilled in the art that the scope of the present invention is not limited to these Examples.

Example 1. Preparation of Gelatin Oil Capsules 1-1. Experimental Groups 1

Microcapsules comprising gelatin, a natural polymer, and an oil were prepared by the same method as shown in FIG. 1.

Specifically, a gelatin solution was prepared by mixing 1.5 g of gelatin (pig, 300 bloom, type A) and 50 ml of deionized water, and then heating the mixture to 70° C., thereby completely melting gelatin. A natural polymer solution was prepared by mixing 1.5 g of Arabic gum and 50 ml of deionized water, and then maintaining the mixture at 70° C., thereby completely melting Arabic gum. After adding 24 g of squalane (hydrogenated poly-1-decene, Puresyn 4) as an oil to the gelatin solution, the squalane was stirred in the gelatin solution at a temperature of 40° C. or more and a rotational speed of 100 to 150 rpm for five minutes by using a stirrer. After adding the natural polymer solution to the stirred gelatin solution, pH of the natural polymer solution was adjusted to a pH value of 3.1 to 3.6 in the stirred gelatin solution by an acidic solution of acetic acid or hydrochloric acid. That is, gelatin and Arabic gum were mixed at a weight ratio of 1:1. After stirring the pH-adjusted solution at a temperature of 35° C. or more for one hour, the pH-adjusted solution was cooled so that the temperature of the pH-adjusted solution became 25° C. by slowly lowering temperature of the pH-adjusted solution. Additionally, after adding water with an amount corresponding to four times the amount of the cooled solution to the cooled solution, and stirring water in the cooled solution, the stirred solution was cooled to 10° C. or less. After moving the cooled solution to a fractional funnel, gelatin oil capsules in an upper layer were separated. After adding an 0.5% glutaraldehyde aqueous solution to the separated gelatin oil capsules, the 0.5% glutaraldehyde aqueous solution was stirred in the separated gelatin oil capsules for one hour. After moving a stirred material containing the gelatin oil capsules to the fractional funnel, the stirred material containing the gelatin oil capsules was cleaned six times with deionized water. After putting completed gelatin oil capsules (gelatin:Arabic gum:hyaluronic acid=1:1:0, Experimental group 1) into deionized water, the completed gelatin oil capsules were stored in the deionized water.

1-2. Experimental Groups 2 to 4

Gelatin oil capsules were prepared by mixing gelatin, Arabic gum, and hyaluronic acid. More specifically, gelatin oil capsules of experimental groups 2 to 4 were prepared in the same method as in the experimental group 1-1, and natural polymer solutions prepared by mixing Arabic gum and hyaluronic acid at weight ratios of Table 1 were used.

TABLE 1

|  | Experimental group 1 | Experimental group 2 | Experimental group 3 | Experimental group 4 |
|---|---|---|---|---|
| Gelatin | 1 | 1 | 1 | 1 |
| Arabic gum | 1 | 0.9 | 0.5 | 0.1 |
| Hyaluronic acid | 0 | 0.1 | 0.5 | 0.9 |

1-3. Experimental Groups 5 to 11

Gelatin oil capsules were prepared by adding an oil thickener, and types and concentrations of the oil thickener are shown in Table 2.

TABLE 2

|  | Types of oil thickener | Concen- tration (%) | Temperature (° C.) |
|---|---|---|---|
| Experimental group 5 | Bentone gel | 10 | 80 |
| Experimental group 6 | Versagel ME 750 | 10 | 80 |
| Experimental group 7 | Rheopearl TT | 10 | 80 |
| Experimental group 8 | Rheopearl KL | 10 | 80 |
| Experimental group 9 |  | 7 | 80 |
| Experimental group 10 |  | 5 | 80 |
| Experimental group 11 |  | 2 | 80 |

Specifically, a gelatin solution was prepared by mixing 3 g of gelatin (pig, 300 bloom, type A) and 100 ml of deionized water, and then heating the mixture to 70° C., thereby completely melting gelatin. A natural polymer solution was prepared by mixing 3 g of Arabic gum and 100 ml of deionized water, and then maintaining the mixture at 70° C., thereby completely melting Arabic gum. After adding oil thickeners corresponding to respective experimental groups in amounts of weight percentages (concentrations) disclosed in Table 2 along with 24.54 g of squalane (hydrogenated poly-1-decene, Puresyn 4) as an oil to the gelatin solution, the oil thickeners and the squalane were stirred in the gelatin solution at a temperature of 45° C. or more and a rotational speed of 100 to 150 rpm for five minutes by using a stirrer. After adding the natural polymer solution to the stirred gelatin solution, pH of the natural polymer solution was adjusted to a pH value of 3.1 to 3.6 in the stirred gelatin solution by an acidic solution of acetic acid or hydrochloric acid. After stirring the pH-adjusted solution at a temperature of 35° C. or more for one hour, the pH-adjusted solution was cooled so that the temperature of the pH-adjusted solution became 25° C. by slowly lowering temperature of the pH-adjusted solution. Additionally, after adding water with an amount corresponding to four times the amount of the cooled solution to the cooled solution, and stirring water in the cooled solution, the stirred solution was cooled to 10° C. or less. After moving the cooled solution to a fractional funnel, gelatin oil capsules in an upper layer were separated. After adding an 0.5% glutaraldehyde aqueous solution to the separated gelatin oil capsules, the 0.5% glutaraldehyde aqueous solution was stirred in the separated gelatin oil capsules for one hour. After moving a stirred material containing the gelatin oil capsules to the fractional funnel, the stirred material containing the gelatin oil capsules was cleaned six times with deionized water. After putting completed gelatin oil capsules into deionized water, the completed gelatin oil capsules were stored in the deionized water.

Example 2. Measuring Elastic Moduli of Gelatin Oil Capsules

Elastic moduli of gelatin oil capsules of the experimental groups 1 to 4 were measured. Specifically, the gelatin oil capsules were disposed between two flat plates with a radius of 20 mm in a state that the gelatin oil capsules were spaced apart from one another at intervals of 1,000 μm. The elastic moduli of the gelatin oil capsules were analyzed by fixing strain to 0.01 at room temperature, and using a rotating rheometer (TA Instruments, AR 1500ex) in a range of 0.01 to 5 Hz. Results of measuring the elastic moduli of the gelatin oil capsules are shown in FIG. 2.

As shown in FIG. 2, it is confirmed that, when preparing the gelatin oil capsules, elasticities of the gelatin oil capsules are increased in case of replacing a portion of Arabic gum with hyaluronic acid. Particularly, it is confirmed that elasticities are remarkably increased in the experimental group 3 in which Arabic gum and hyaluronic acid are mixed at a weight ratio of 1:1, and the experimental group 4 in which Arabic gum and hyaluronic acid are mixed at a weight ratio of 1:9.

Example 3. Co-Culturing Gelatin Oil Capsules and Cardiomyocytes

The gelatin oil capsules of the experimental group 4 prepared in Example 1 and human derived cardiomyocytes (iCell Cardiomyocytes, CMC-100-010-001, USA, Cellular Dynamics International) were co-cultured. Specifically, in order to use the gelatin oil capsules as a cell culture, the capsules were stirred in the PBS for five minutes after immersing the capsules in PBS. After finishing the stirring process, replacing the used PBS with new PBS, and additionally performing the stirring process, these processes were repeated 2 to 3 times. After finishing the stirring process, removing the PBS, and moving the gelatin oil capsules to plating mediums (plating medium 50%, Fetal Bovine Serum (FBS) (Hyclone, SH30919.03, USA) 10%), the gelatin oil capsules were stored at 4° C. in the plating mediums for 24 hours.

In order to perform a co-culturing process, cardiomyocytes were treated with trypsin and floated as single cells. After inactivating trypsin with a serum-containing medium, and centrifuging the inactivated trypsin, the cardiomyocytes were obtained. After adding a new medium to the obtained cells, and refloating the new medium-added cells, the refloated cells was counted. The counted cells were prepared so that the cells were contained in a high concentration in a medium of 200 μl. After moving the gelatin oil capsules, i.e., cell culture to a 15 ml conical tube, a culture medium was added to the cell culture to the extent that the cell culture was wetted with the culture medium. After inoculating prepared cardiomyocytes into a conical tube containing the cell culture and the medium, the cardiomyocytes inoculated into the conical tube were cultured. The culturing process was performed overnight in an incubator maintaining a temperature of 37° C. and 5% of $CO_2$, and the incubator was tapped several times at intervals of 15 to 30 minutes so that settled cells could be floated again. After moving the culturing process completed cardiomyocyte-cell culture to a culture container with a low cell adhesive force, the cardiomyocyte-cell culture was observed by an optical microscope, a scanning electron microscope (SEM), and a transmission electron microscope (TEM). The cardiomyocyte-cell culture was observed by the same method also in the gelatin oil capsules of the experimental groups 2 to 4. Results of observing the cardiomyocyte-cell culture are shown in FIGS. 3 and 4.

As shown in FIG. 3, it is confirmed that cardiomyocytes are concentrated around gelatin oil capsules, i.e., cell cultures of the experimental groups 1 to 4. On the other hand, it is observed that cells are scattered on plates in a control group in which the cell culture is not used.

As shown in FIG. 4, it is confirmed that cardiomyocytes are adhered to the cell cultures of the experimental groups 1 to 4, and spheres are formed by the cultured cells. Particularly, it is confirmed that cardiomyocytes of the experimental groups 2 to 4 using gelatin, Arabic gum, and hyaluronic acid during the preparation of cell cultures exhibit a form similar to that of mature muscle cells.

Example 4. Analyzing Cellular Viabilities of Co-Cultured Cardiomyocytes

After culturing the cardiomyocytes for up to 42 days at intervals of 1 week from the 4th day of culturing so as to check viabilities of cardiomyocytes co-cultured using the experimental group 4 prepared in Example 1, the viabilities of the cardiomyocytes were checked through live-dead assay (abcam, ab65470). After performing the live-dead assay in accordance with the manual of a manufacturer, results of the assay are shown in FIG. 5.

As shown in FIG. 5, green fluorescence refers to live cells, red fluorescence refers to dead cells, and it is confirmed that most cells are alive regardless of the number of inoculated cells or the period of culturing.

Example 5. Observing Co-Cultured Cardiomyocytes Using a Transmission Electron Microscope Cardiomyocytes co-cultured with the experimental group 4 prepared in Example 1 were observed by using a transmission electron microscope (TEM). Specifically, cardiomyocytes were co-cultured and prepared by the same method as in Example 3-1 in experimental groups, and the cardiomyocytes were co-cultured by a conventionally known method in the control group. After observing the cultured cardiomyocytes by the TEM, results of the observation are shown in FIGS. 6 and 7.

other hand, a plurality of mature muscle cells are observed in the experimental groups, and it is confirmed that spheres are formed by the cultured cells. As it is confirmed from the foregoing results that using gelatin oil capsules as a cell culture not only forms the spheres, but also matures the cardiomyocytes, spherical cardiomyocytes may be used as an artificial myocardial structure.

Next, the co-cultured cardiomyocytes were observed by the TEM so as to check the maturation degree of intracellular organelles of the co-cultured cardiomyocytes. Specifically, the co-cultured cardiomyocytes were immobilized in a low temperature environment of 4° C. by using 2.5% glutaraldehyde in PBS. The immobilized cells were washed with a 0.1 M phosphate buffer solution with a pH value of 7.4 for 10 to 20 minutes. A postprocess included carrying out a reaction process using 1% $OsO_4$ (osmic acid) for about one hour, and performing a washing process again by using the 0.1 M phosphate buffer solution with a pH value of 7.4. In order to remove moisture within samples, 50%, 70%, 80%, 95%, and 100% ethyl alcohols were dehydrated from low concentrations to high concentrations within five minutes. After cutting the samples to 1 μm by using an ultramicrotome, and moving the cut samples to slide glasses, the cut samples were adhered and fixated to the hot plates while extending the samples on hot plates with a temperature of 80° C. After passing the samples adhered and fixated to the hot plates through an electron staining process, and observing the samples passing through the electron staining process, results of the observation are shown in FIG. 7.

As shown in FIG. 7, some myofibrils and mitochondria are observed in two weeks after performing the culturing process, and mature mitochondria and myofibrils are observed from the fifth week compared to the second week. Furthermore, it is confirmed that polynucleated cells and solid junction that may be seen from mature cardiomyocytes are formed.

Example 6. Comparing Properties of Gelatin Oil Capsules Depending on the Addition of an Oil Thickener After comparing viscosities, forms, and whether or not to form an emulsion of gelatin oil capsules of the experimental groups 5 to 11, comparison results are shown in Table 3.

TABLE 3

| | Viscosity (at room temperature) | Form | Emulsion formation | Others |
|---|---|---|---|---|
| Experimental group 5 | Low | Particles are formed, and have dull brown color | — | The viscosity is very low |
| Experimental group 6 | Low | Transparent | — | |
| Experimental group 7 | High | Formation of a gel that is dull and thixotropic | — | |
| Experimental group 8 | Very high | Formation of a gel that is dull and hard | — | The viscosity is very high |
| Experimental group 9 | High | Formation of a gel that is dull and hard | Nonexistence | The emulsion formation efficiency is low |
| Experimental group 10 | High | Formation of a gel that is dull and hard | Existence | Appropriate |
| Experimental group 11 | Low | Formation of a gel that is dull and hard | Existence | The viscosity enhancement effect is low |

As shown in FIGS. 6 and 7, a plurality of immature cardiomyocytes are observed in the control group. On the As shown in Table 3, it may be seen that properties of the gelatin oil capsules are changed depending on the addition of an oil thickener. Particularly, it may be seen that the gelatin oil capsules of the experimental group 10 using Rheopearl KL (Dextrin Palmitate) with 5% concentration as the oil thickener have a high viscosity at room temperature, not only form a gel that is dull and hard, but also form an emulsion.

Example 7. Comparing Retention Properties of Gelatin Oil Capsules Depending on Whether or Not to Add an Oil Thickener Retention properties of gelatin oil capsules of the experimental group 4 to which an oil thickener was not added under physical conditions and those of gelatin oil capsules of the experimental group 10 to which the oil thickener was added were compared. Specifically, a partial pressure was applied to each of the foregoing gelatin oil capsules by using a needle. Retention properties of the pressure-applied gelatin oil capsules were observed. Results of comparing the retention properties of the gelatin oil capsules are shown in FIG. 8.

As shown in FIG. 8, it is confirmed that, although a partial pressure is applied to the gelatin oil capsules of the experimental group 10 to which the oil thickener is added, the gelatin oil capsules of the experimental group 10 are not burst while maintaining the smooth state. Moreover, it is confirmed that the gelatin oil capsules of the experimental group 10 to which the oil thickener is added maintain their shapes without spreading oil inside the gelatin oil capsules even after the gelatin oil capsules are burst by continuous stimulation. On the other hand, it may be seen that the gelatin oil capsules of the experimental group 4 to which an oil thickener is not added are burst due to the pressure applied thereto, and it is confirmed that oil inside the gelatin oil capsules is flown out and spread. The foregoing results mean that adding the oil thickener during the preparation of the gelatin oil capsules enhances the retention properties of prepared capsules. Furthermore, as oil inside oil thickener-added gelatin oil capsules maintains its form even after the capsules are burst, it may be seen that oxygen may be continuously supplied to the cells under culturing although the gelatin oil capsules are damaged when culturing cells by using the oil thickener-added gelatin oil capsules.

Overall, the present inventors have developed gelatin oil capsules, and have confirmed that mechanical properties and retention properties of the gelatin oil capsules are remarkably enhanced when preparing the gelatin oil capsules by mixing gelatin, Arabic gum, hyaluronic acid, and an oil thickener during preparation of the gelatin oil capsules. Accordingly, gelatin oil capsules according to the present invention may be diversely used in the fields of microcarriers, cell cultures, and co-culture systems.

The invention claimed is:

1. A preparation method of microcapsules, the preparation method comprising:
   a step (a) of preparing a gelatin solution containing gelatin, a natural oil, and dextrin palmitate as an oil thickener;
   a step (b) of preparing a natural polymer solution;
   a step (c) of mixing the gelatin solution of the step (a) and the natural polymer solution of the step (b);
   a step (d) of adjusting pH of the mixture prepared in the step (c); and
   a step (e) of cooling the pH-adjusted mixture of the step (d) to form microcapsules, each microcapsule having a wall containing gelatin and the natural polymer, surrounding a core containing the natural oil thickened with dextrin palmitate,
   wherein the oil thickener is contained in an amount of 5 weight % with respect to the weight of the oil,
   wherein the natural polymer is a mixture of arabic gum and hyaluronic acid, and
   wherein the arabic gum and the hyaluronic acid are mixed at a weight ratio of 1:1 to 1:9.

2. The preparation method of claim 1, wherein the natural oil is one or more selected from the group consisting of olive oil, camellia oil, castor oil, palm oil, Jojoba oil, almond oil, grapeseed oil, herbal oil, rose oil, coconut oil, moringa oil, rice bran oil, apricot kernel oil, sunflower oil, meadowfoam seed oil, Abyssinian oil, and squalane.

3. The preparation method of claim 1, wherein the dextrin palmitate is the only oil thickener present.

4. The preparation method of claim 1, wherein the microcapsules are suitable for use as carriers for mammalian cell culture.

5. The preparation method of claim 4, wherein the microcapsules are suitable to support cell aggregation and the formation of spheroids in the mammalian cell culture.

* * * * *